(12) United States Patent
Shameli et al.

(10) Patent No.: US 11,633,083 B2
(45) Date of Patent: Apr. 25, 2023

(54) 3D SCANNING OF NASAL TRACT WITH DEFLECTABLE ENDOSCOPE

(71) Applicant: Acclarent, Inc., Irvine, CA (US)

(72) Inventors: Ehsan Shameli, Irvine, CA (US); Fatemeh Akbarian, Rancho Palos Verdes, CA (US)

(73) Assignee: Acclarent, Inc., Irvine, CA (US)

( * ) Notice: Subject to any disclaimer, the term of this patent is extended or adjusted under 35 U.S.C. 154(b) by 455 days.

(21) Appl. No.: 16/666,490

(22) Filed: Oct. 29, 2019

(65) Prior Publication Data
US 2020/0196851 A1     Jun. 25, 2020

Related U.S. Application Data

(60) Provisional application No. 62/782,608, filed on Dec. 20, 2018.

(51) Int. Cl.
| | |
|---|---|
| *A61B 1/00* | (2006.01) |
| *A61B 1/233* | (2006.01) |
| *A61B 1/05* | (2006.01) |
| *A61B 1/005* | (2006.01) |

(Continued)

(52) U.S. Cl.
CPC ...... *A61B 1/000094* (2022.02); *A61B 1/0051* (2013.01); *A61B 1/00158* (2013.01); *A61B 1/00194* (2022.02); *A61B 1/05* (2013.01); *A61B 1/0605* (2022.02); *A61B 1/0655* (2022.02); *A61B 1/0676* (2013.01); *A61B 1/0684* (2013.01); *A61B 1/233* (2013.01); *A61B 5/062* (2013.01)

(58) Field of Classification Search
None
See application file for complete search history.

(56) References Cited

U.S. PATENT DOCUMENTS

| | | |
|---|---|---|
| 7,720,521 B2 | 5/2010 | Chang et al. |
| 8,199,988 B2 | 6/2012 | Marshall et al. |
| 8,821,158 B1 | 9/2014 | Hultgren |

(Continued)

FOREIGN PATENT DOCUMENTS

| | | |
|---|---|---|
| DE | 102010009884 A1 | 9/2011 |
| DE | 102012214219 A1 | 2/2014 |
| WO | WO 2017/125926 A2 | 7/2017 |

OTHER PUBLICATIONS

International Search Report and Written Opinion dated Mar. 17, 2020 for International Application No. PCT/IB2019/060798, 15 pages.

*Primary Examiner* — John P Leubecker
*Assistant Examiner* — Minqiao Huang
(74) *Attorney, Agent, or Firm* — Frost Brown Todd LLP

(57) ABSTRACT

An apparatus includes a shaft, an imaging head, and a processor. The shaft includes a distal end sized to fit through a human nostril into a human nasal cavity. The imaging head includes an image sensor assembly, a plurality of light sources, and a plurality of collimators. At least some of the light sources are positioned adjacent to the image sensor assembly. Each collimator is positioned over a corresponding light source of the plurality of light sources. The processor is configured to activate the light sources in a predetermined sequence. The image sensor assembly is configured to capture images of a surface illuminated by the light sources as the light sources are activated in the predetermined sequence.

20 Claims, 11 Drawing Sheets

(51) Int. Cl.
   *A61B 1/06* (2006.01)
   *A61B 5/06* (2006.01)

(56) References Cited

U.S. PATENT DOCUMENTS

| | | | |
|---|---|---|---|
| 9,107,573 B2* | 8/2015 | Birnkrant | A61B 1/005 |
| 2001/0051802 A1* | 12/2001 | Woloszko | A61B 18/1482 |
| | | | 604/35 |
| 2011/0004057 A1 | 1/2011 | Goldfarb et al. | |
| 2014/0364725 A1 | 12/2014 | Makower | |
| 2016/0008083 A1 | 1/2016 | Kesten et al. | |
| 2016/0073853 A1 | 3/2016 | Venkatesan et al. | |
| 2016/0135672 A1 | 5/2016 | Spinnler et al. | |
| 2018/0116509 A1* | 5/2018 | Myung | A61B 3/10 |
| 2018/0303550 A1* | 10/2018 | Altmann | A61B 34/10 |
| 2018/0310886 A1 | 11/2018 | Salazar et al. | |
| 2019/0015645 A1 | 1/2019 | Matlock et al. | |
| 2019/0388194 A1* | 12/2019 | Atiya | G02B 27/4222 |

\* cited by examiner

3D SCANNING OF NASAL TRACT WITH DEFLECTABLE ENDOSCOPE

PRIORITY

This application claims priority to U.S. Provisional Pat. App. No. 62/782,608, entitled "3D Scanning of Nasal Tract with Deflectable Endoscope," filed Dec. 20, 2018, the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guidewire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein.

While a conventional endoscope may be used to provide visualization within an anatomical passageway, it may also be desirable to provide additional visual confirmation of the proper positioning of a dilation catheter or some other instrument before performing an operation with that instrument. This may be done using image-guided surgery (IGS), which is a technique where a computer is used to obtain a real-time correlation of the location of an instrument that has been inserted into a patient's body to a set of preoperatively obtained images (e.g., a CT or MRI scan, 3-D map, etc.) so as to superimpose the current location of the instrument on the preoperatively obtained images. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) mounted thereon are used to perform the procedure while the sensors send data to the computer indicating the current position of each surgical instrument. The computer correlates the data it receives from the instrument-mounted sensors with the digital map that was created from the preoperative tomographic scan. The tomographic scan images are displayed on a video monitor along with an indicator (e.g., cross hairs or an illuminated dot, etc.) showing the real time position of each surgical instrument relative to the anatomical structures shown in the scan images. In this manner, the surgeon is able to know the precise position of each sensor-equipped instrument by viewing the video monitor even if the surgeon is unable to directly visualize the instrument itself at its current location within the body.

While several systems and methods have been made and used to generate digital maps or models for use in IGS navigated ENT procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
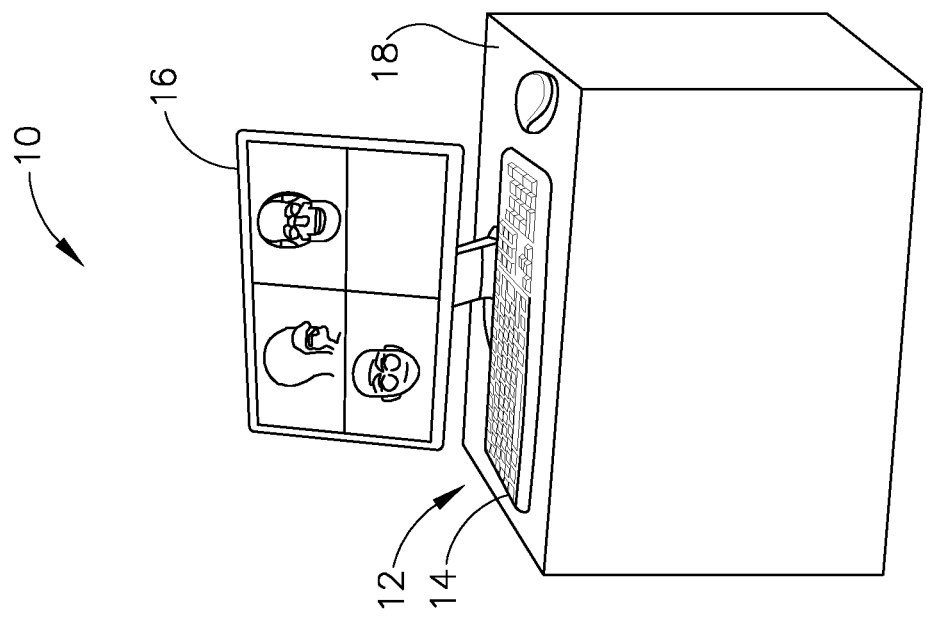
FIG. 1 depicts a schematic view of an exemplary surgery navigation system being used on a patient seated in an exemplary medical procedure chair.
Figure 1:
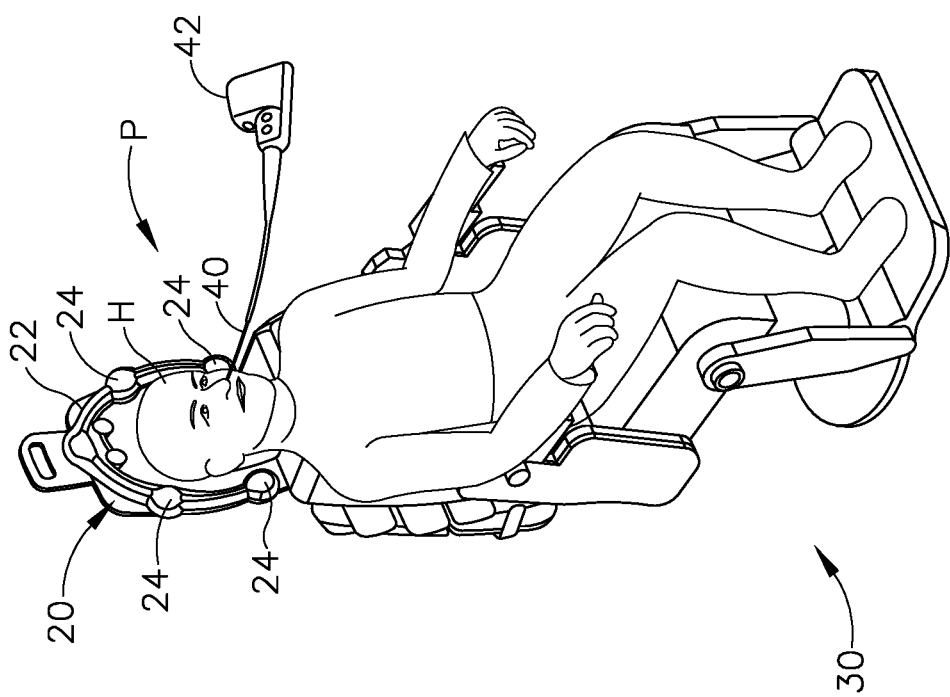

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Image Guided Surgery Navigation System

When performing a medical procedure within a head (H) of a patient (P), it may be desirable to have information regarding the position of an instrument within the head (H) of the patient (P), particularly when the instrument is in a location where it is difficult or impossible to obtain an endoscopic view of a working element of the instrument within the head (H) of the patient (P). FIG. 1 shows an exemplary IGS navigation system (10) enabling an ENT procedure to be performed using image guidance. In addition to or in lieu of having the components and operability described herein IGS navigation system (10) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein; and U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein.

IGS navigation system (10) of the present example comprises a field generator assembly (20), which comprises set of magnetic field generators (24) that are integrated into a horseshoe-shaped frame (22). Field generators (24) are operable to generate alternating magnetic fields of different frequencies around the head (H) of the patient (P). A 3D imaging endoscope (40) is inserted into the head (H) of the patient (P) in this example. In the present example, frame (22) is mounted to a chair (30), with the patient (P) being seated in the chair (30) such that frame (22) is located adjacent to the head (H) of the patient (P). By way of example only, chair (30) and/or field generator assembly (20) may be configured and operable in accordance with at least some of the teachings of U.S. Pat. Pub. No. 2018/0310886, entitled "Apparatus to Secure Field Generating Device to Chair," published Nov. 1, 2018, issued as U.S. Pat. No. 10,561,370 on Feb. 18, 2020, the disclosure of which is incorporated by reference herein.

IGS navigation system (10) of the present example further comprises a processor (12), which controls field generators (24) and other elements of IGS navigation system (10). For instance, processor (12) is operable to drive field generators (24) to generate alternating electromagnetic fields; and process signals from endoscope (40) to determine the location of a position sensor (50) in endoscope (40) within the head (H) of the patient (P). Processor (12) comprises a processing unit communicating with one or more memories. Processor (12) of the present example is mounted in a console (18), which comprises operating controls (14) that include a keypad and/or a pointing device such as a mouse or trackball. A physician uses operating controls (14) to interact with processor (12) while performing the surgical procedure.

Endoscope (40) of the present example includes a position sensor (50) that is responsive to positioning within the alternating magnetic fields generated by field generators (24). A coupling unit (42) is secured to the proximal end of endoscope (40) and is configured to provide communication of data and other signals between console (18) and endoscope (40). Coupling unit (42) may provide wired or wireless communication of data and other signals.

In the present example, position sensor (50) of endoscope (40) comprises at least one coil at the distal end (48) of endoscope (40). When such a coil is positioned within an alternating electromagnetic field generated by field generators (24), the alternating magnetic field may generate electrical current in the coil, and this electrical current may be communicated along the electrical conduit(s) in endoscope (40) and further to processor (12) via coupling unit (42). This phenomenon may enable IGS navigation system (10) to determine the location of distal end (48) of endoscope (40) within a three-dimensional space (i.e., within the head (H) of the patient (P), etc.). To accomplish this, processor (12) executes an algorithm to calculate location coordinates of distal end (48) of endoscope (40) from the position related signals of the coil(s) in position sensor (50) endoscope (40).

Processor (12) uses software stored in a memory of processor (12) to calibrate and operate IGS navigation system (10). Such operation includes driving field generators (24), processing data from endoscope (40), processing data from operating controls (14), and driving display screen (16). In some implementations, operation may also include monitoring and enforcement of one or more safety features or functions of IGS navigation system (10). Processor (12) is further operable to provide video in real time via display screen (16), showing the position of distal end (48) of endoscope (40) in relation to a video camera image of the patient's head (H), a CT scan image of the patient's head (H), and/or a computer-generated three-dimensional model of the anatomy within and adjacent to the patient's nasal cavity. Display screen (16) may display such images simultaneously and/or superimposed on each other during the surgical procedure. Such displayed images may also include graphical representations endoscope (40) in the patient's head (H), such that the operator may view the virtual rendering of endoscope (40) at its actual location in real time. By way of example only, display screen (16) may provide images in accordance with at least some of the teachings of U.S. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein. Endoscopic images that are being captured by endoscope (40), as described below, may also be provided on display screen (16).

The images provided through display screen (16) may help guide the operator in maneuvering and otherwise manipulating endoscope (40) within the patient's head (H). It should also be understood that various other kinds of surgical instruments (e.g., guidewires, guide catheters, dilation catheters, suction instruments, shaver instruments, etc.) may incorporate a position sensor like position sensor (50) of endoscope (40). As described above in the context of endoscope (40), IGS navigation system (10) may enable an operator to view the position of the sensor-equipped instrument within the head (H) of the patient (P) in real time, such as by superimposing a position indicator on dynamically-changing views from a set of preoperatively obtained images (e.g., CT scans, etc.) of the head (H) of the patient (P).

II. Exemplary 3D Mapping with Endoscope

In some instances, it may be beneficial to provide an operator with a three-dimensional view of surfaces of anatomical structures in the head (H) of a patient (P). As noted above, IGS navigation system (10) may include preoperatively obtained images of anatomical structures in the head (H) of the patient (P). In conventional versions of IGS navigation system (10), such images may fail to include a three-dimensional view of surfaces of anatomical structures in the head (H) of a patient (P). For instance, in conventional versions of IGS navigation system (10), the preoperatively obtained images may just include CT scan images, two-dimensional views of surfaces of anatomical structures in the head (H) of a patient (P), or other kinds of images that do not constitute three-dimensional views of surfaces of anatomical structures in the head (H) of a patient (P). In instances where IGS navigation system (10) can superimpose real-time instrument position indications in relation to preoperatively obtained three-dimensional views of surfaces of anatomical structures in the head (H) of a patient (P), the operator may have a better sense of the real-time position of instruments in relation to the anatomical structures in the head (H) of the patient (P).

To the extent that a conventional IGS navigation system (10) is capable of generating or otherwise processing a three-dimensional digital model of anatomical structures in the head (H) of a patient (P), such a three-dimensional digital model may lack a three-dimensional optical view of surfaces of anatomical structures in the head (H) of a patient (P) as part of the data set that is used to generate the three-dimensional digital model. Thus, it may be beneficial to include a three-dimensional optical view of surfaces of anatomical structures in the head (H) of a patient (P) as part of the data set that is used to generate a three-dimensional digital model. Such a three-dimensional optical view of surfaces of anatomical structures in the head (H) of a patient (P) may be used to refine the data on the surfaces that is obtained through other imaging techniques such as CT scanning, etc.

Those skilled in the art will recognize that the nasal cavity and adjacent regions within the head (H) of a patient (P) is a relatively small space with various tortuous pathways and obstacles. Thus, in order to maximize access for an instrument within the nasal cavity and adjacent regions within the head (H) of a patient (P), it is advantageous to provide such an instrument with a relatively small form factor and at least some degree of flexibility. It may be further beneficial to provide such an instrument with steerability, such that the operator may actively bend or otherwise move the distal portion of the instrument relative to the proximal portion of the instrument, thereby allowing the distal portion of the instrument to more actively maneuver around anatomical structures to reach spaces that would otherwise be inaccessible to a fully-rigid instrument.

The following description relates to an exemplary form of endoscope (40) that may be used to obtain three-dimensional optical views of surfaces of anatomical structures in the head (H) of a patient (P), including anatomical structures in the nasal cavity and adjacent regions. Such views may be obtained before a medical procedure is performed on the patient (P), such that the views may be later provided to an operator via IGS navigation system (10). Alternatively, such views may be provided to an operator in any other suitable fashion; or be used in any other suitable way. Moreover, as will be described in greater detail below, the three-dimensional optical views obtained through endoscope (40) may be used to generate a three-dimensional digital model of the surfaces of anatomical structures in the head (H) of a patient (P). In some such cases, the three-dimensional optical views obtained through endoscope (40) are combined with views obtained through other imaging means (e.g., CT scanning, etc.) to generate a composite three-dimensional digital model. This digital model may be utilized by IGS navigation system (10) to provide an operator with refined image-guided surgery capabilities. In some other instances, the three-dimensional images from endoscope (40) and/or associated three-dimensional digital model are utilized in some other fashion, without necessarily involving an IGS navigation system (10) in any way.

Figure 2:
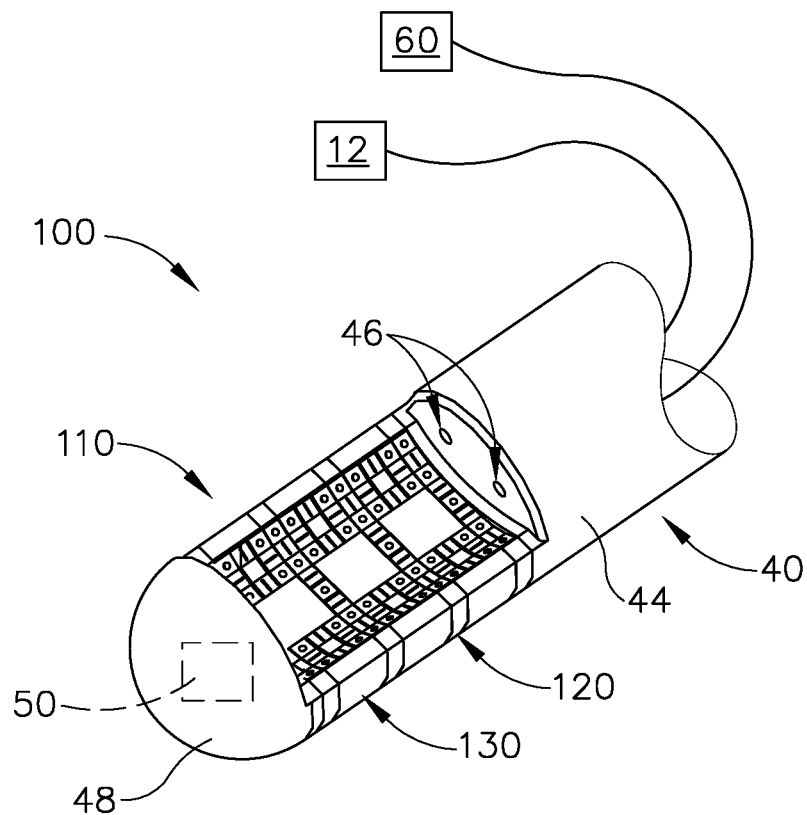
FIG. 2 depicts a perspective view of a distal end of an exemplary 3D imaging endoscope that may be used in conjunction with the navigation system of FIG. 1.
Figure 3:
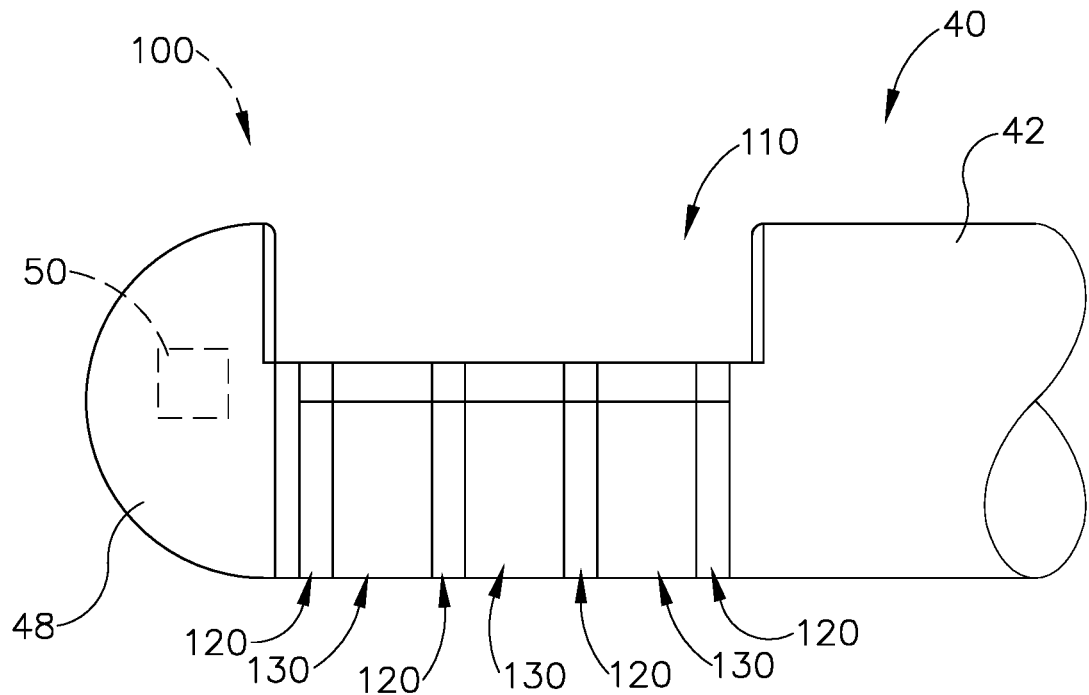
FIG. 3 depicts a side elevational view of the distal end of the endoscope of FIG. 2.
Figure 4:
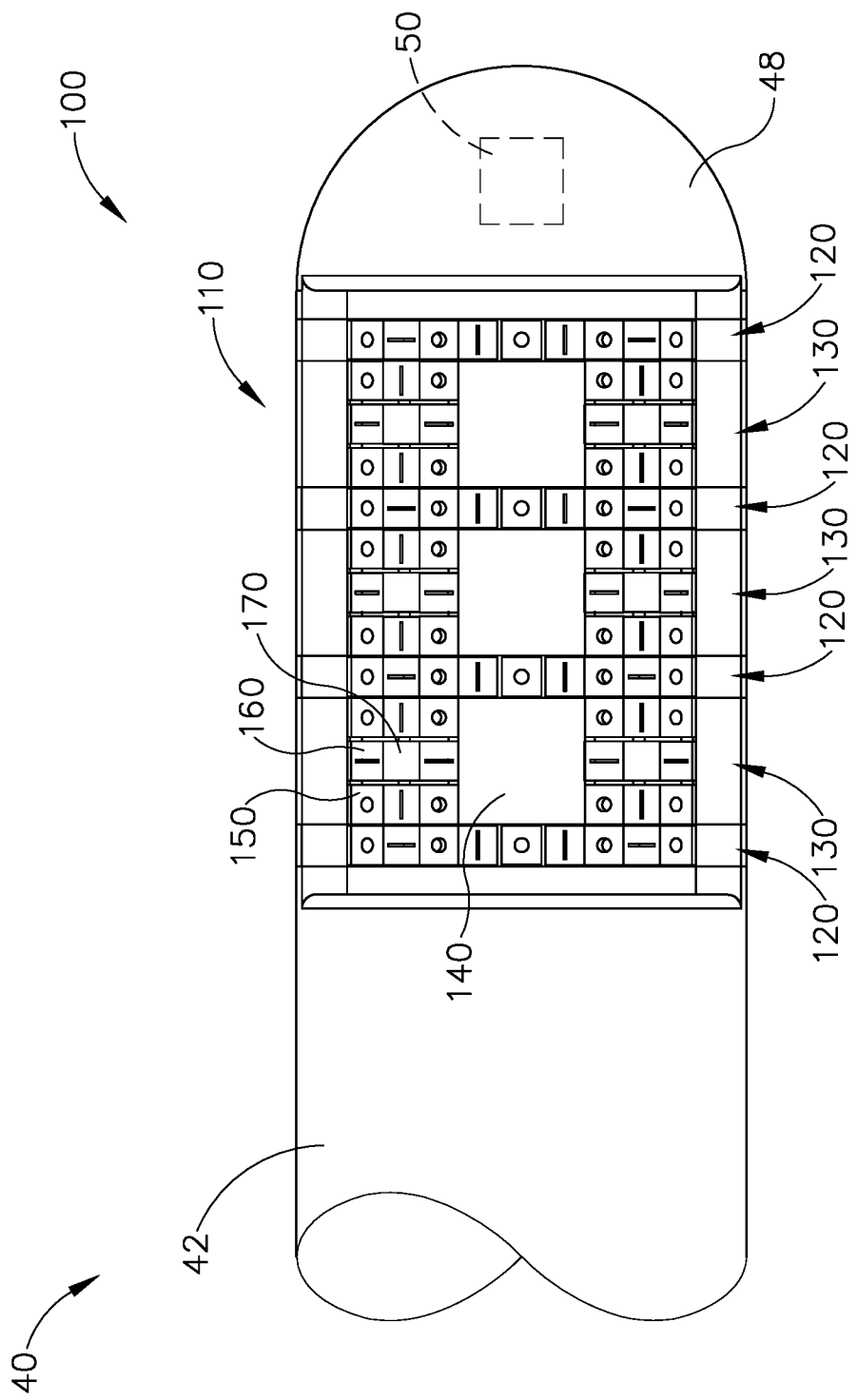
FIG. 4 depicts a top plan view of the distal end of the endoscope of FIG. 2.

As shown in FIGS. 2-4, endoscope (40) of the present example includes a shaft (42) with an imaging head (100) at the distal end of shaft (42) and a closed, atraumatic distal tip (48). In the present example, at least a portion of shaft (42) is flexible. In some versions, a distal portion of shaft (42) is steerable, such that an operator may selectively deform shaft to actively reorient imaging head (100) along different axes relative to the longitudinal axis of the proximal portion of shaft (42). By way of example only, endoscope (40) may include a pull wire or other device to provide controlled deflection of imaging head (100). By way of further example only, such steering may be provided in accordance with at least some of the teachings of U.S. patent application Ser. No. 16/032,471, entitled "Adjustable Instrument for Dilation of Anatomical Passageway," filed Jul. 11, 2018, issued as U.S. Pat. No. 10,874,839 on Dec. 29, 2020, the disclosure of which is incorporated by reference herein.

Imaging head (100) includes a plurality of alternating, longitudinally-stacked subassemblies (120, 130) proximal to distal tip (48). Subassemblies (120, 130) define a lateral notch or recess (110) proximal to distal tip (48). As shown in FIG. 2, shaft (42) includes a pair of distally-presented ports (46) positioned at the proximal end of recess (110). Ports (46) are coupled with a fluid source (60) that is operable to provide a washing fluid (e.g., saline, etc.) to ports (46). Ports (46) are thus operable to wash away debris from imaging head (100) during use of endoscope (40). In some variations, imaging head (100) further includes a wiper or other element to help clear debris, etc., from imaging head (100). Other suitable ways in which imaging head (100) may be kept substantially clear of debris will be apparent to those skilled in the art in view of the teachings herein. Some variations may omit ports (46). Imaging head (100) of the present example is compact enough to fit within various regions of the nasal cavity and adjacent regions within the head (H) of a patient (P). Imaging head (100) may thus be positioned to observe anatomical structures such as paranasal sinus ostia, the frontal recess, Eustachian tube openings, various regions of nasal turbinates, etc. Such a small size of imaging head (100) may be particularly leveraged advantageously in versions where shaft (42) includes features enabling the operator to selectively steer or deflect imaging head (100) as noted above.

As best seen in FIG. 3, subassemblies (120, 130) are longitudinally stacked adjacent to each other, with a total of four subassemblies (120) and a total of three subassemblies (130); and with subassemblies (120) being at each end of the stack. Variations of endoscope (40) may include any other suitable number of subassemblies (120, 130) in any other suitable arrangement. Moreover, variations of endoscope (40) may integrate the below-described features and functionalities of subassemblies (120, 130) into one single component or in some other arrangement. Other suitable ways in which the below-described features and functionalities of subassemblies (120, 130) may be integrated into imaging head (100) will be apparent to those skilled in the art in view of the teachings herein.

Figure 7:
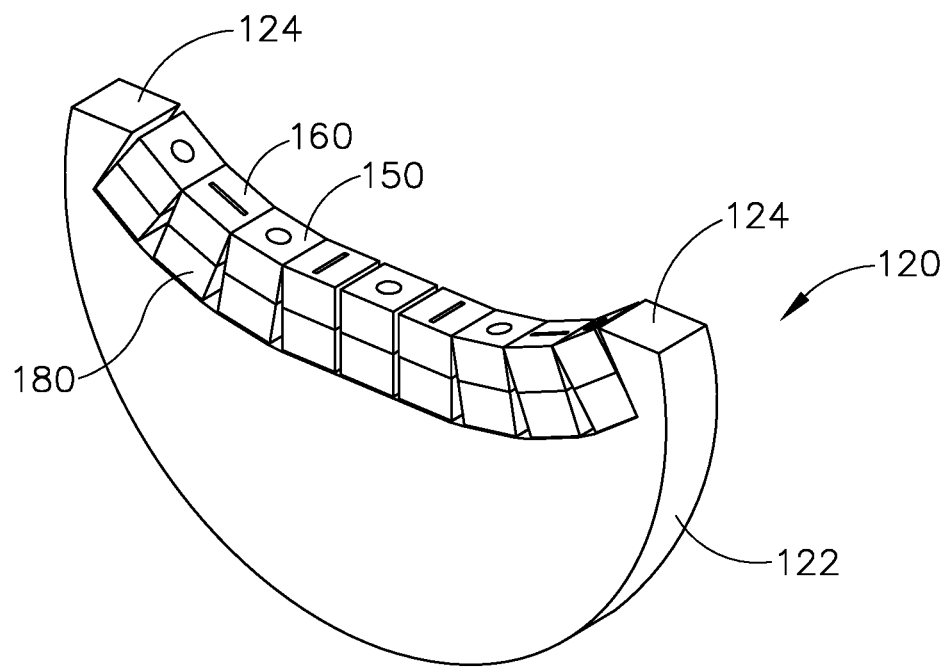
FIG. 7 depicts a perspective view of a first kind of subassembly of the distal end of the endoscope of FIG. 2.
Figure 9:
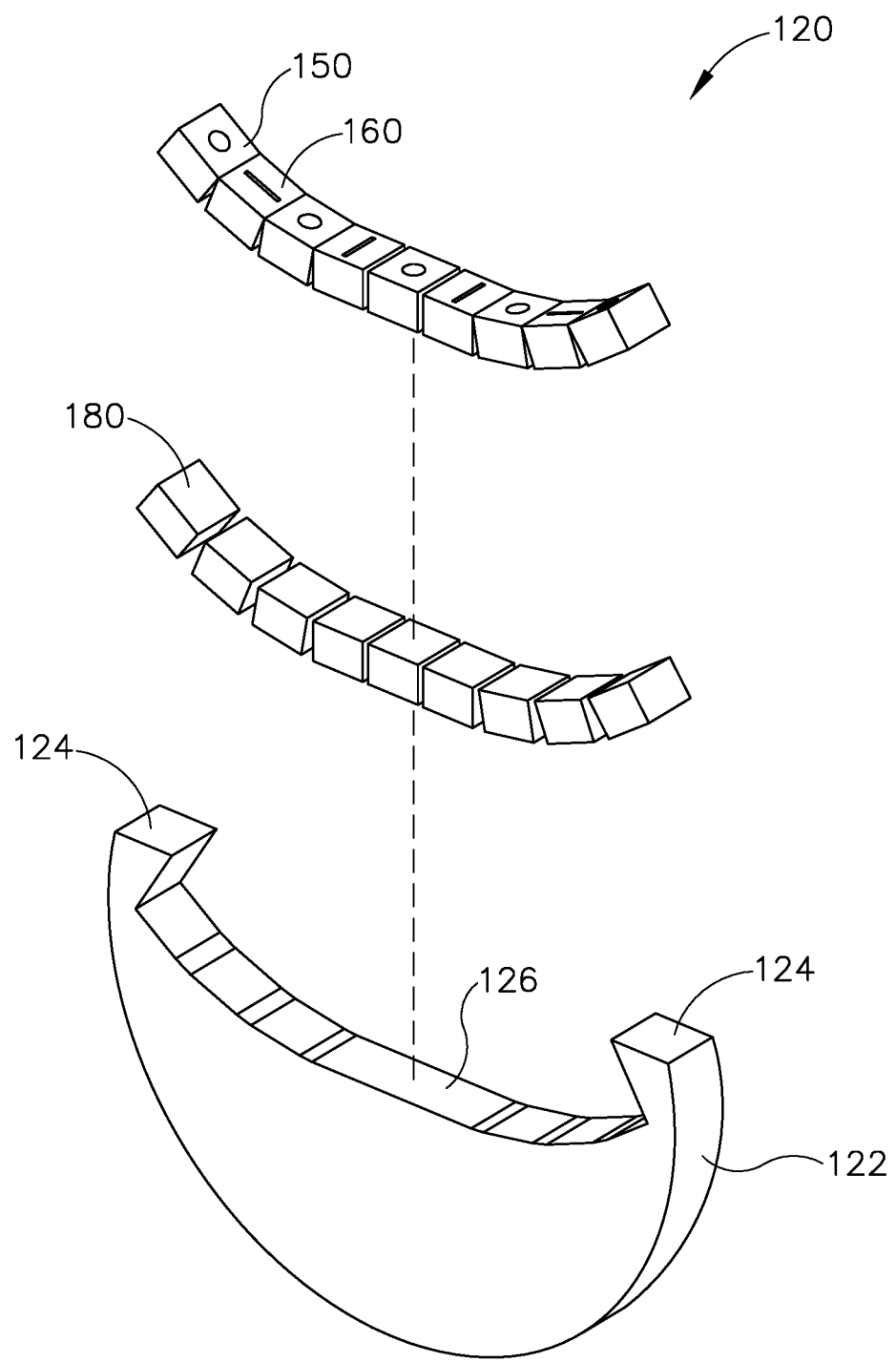
FIG. 9 depicts a partially exploded perspective view of the subassembly of FIG. 7.

As best seen in FIGS. 4, 7, and 9, each subassembly (120) includes a body (122), an array of light sources (180), and an array of collimators (150, 160). Body (122) defines a recessed surface (126) that supports light sources (180). Fingers (124) are positioned at opposing ends of recessed surface (126) to further contain light sources (180) in recessed surface (126). Light sources (180) are operable to emit light independently of each other, such that light sources (180) may be activated in a predetermined pattern as described in greater detail below. Light sources (180) may also be configured to emit light at different wavelengths, thereby providing different colors of visible light or other differences in optical characteristics (e.g., ultraviolet, infrared, etc.). Light sources (180) may also be configured to emit light at different intensities. In some variations, each light source (180) is configured to vary its optical output (e.g., by varying its intensity or wavelength, etc.). In some other variations, each light source (180) has a fixed, predetermined optical output (e.g., constant intensity, constant wavelength, etc.). In some such variations, the optical output of light sources (180) vary among subassembly (120), such that the optical output of one light source (180) in subassembly (120) may be different from the optical output of another light source (180) in subassembly (120). By way of example only, light sources (180) may comprise LEDs. Other suitable forms that light sources (180) may take will be apparent to those skilled in the art in view of the teachings herein. Those skilled in the art will also recognize that light sources (180) of the present example are positioned to project light along a path that is transversely oriented relative to the longitudinal axis of shaft (42).

Figure 5:
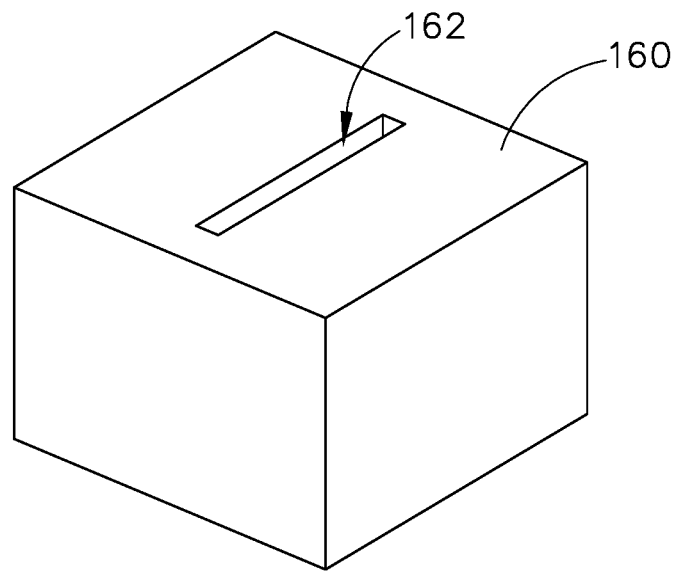
FIG. 5 depicts a perspective view of a rectangular-slit collimator of the distal end of the endoscope of FIG. 2.
Figure 6:
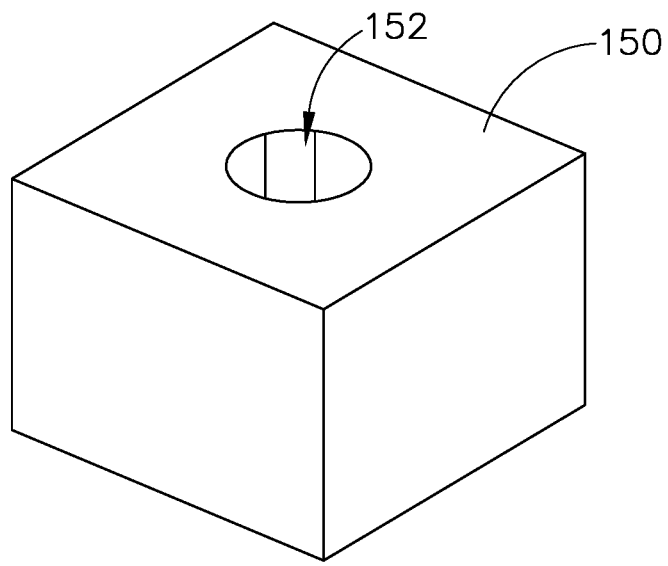
FIG. 6 depicts a perspective view of a circular-slit collimator of the distal end of the endoscope of FIG. 2.

Collimators (150, 160) are positioned over respective light sources (180), such that each light source (180) has one corresponding collimator (150, 160) and vice-versa. Collimators (150, 160) are operable to narrow the light emitted from light sources (180). As best seen in FIG. 5, each collimator (160) has a rectangular slit opening (162). In this example, rectangular slit opening (162) is oriented such that rectangular slit opening (162) is parallel to two side faces of collimator (160) while being perpendicular to two other side faces of collimator (160). In some other versions, rectangular slit (162) opening is oriented obliquely relative to the side faces of collimator (160). As best seen in FIG. 6, each collimator (150) has a circular opening (152). The rectangular slit and circular shapes of openings (162, 152) are merely illustrative examples. Other suitable shapes that may be used will be apparent to those skilled in the art in view of the teachings herein. Referring back to FIGS. 4, 7, and 9, collimators (150, 160) are arranged in an alternating fashion, such that each collimator (150) is positioned adjacent to a collimator (160), such that no collimator (150) is positioned adjacent to another collimator (150), and such that no collimator (160) is positioned adjacent to another collimator (160). Of course, any other suitable relationship may be used as will be apparent to those skilled in the art in view of the teachings herein.

Figure 8:
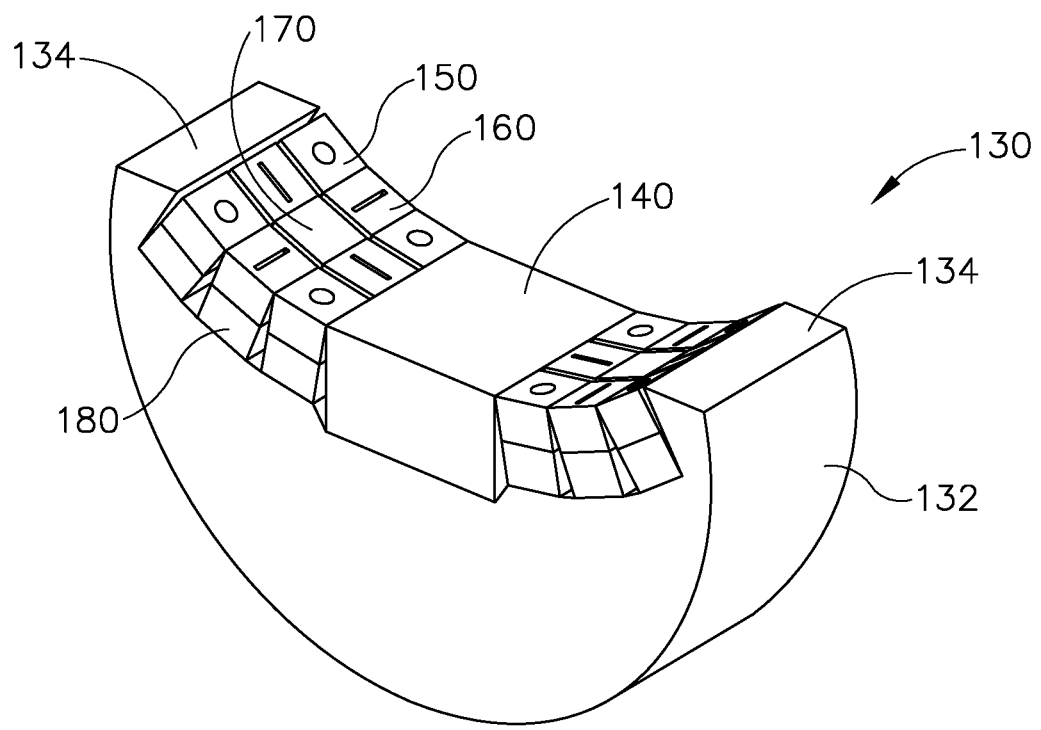
FIG. 8 depicts a perspective view of a second kind of subassembly of the distal end of the endoscope of FIG. 2.
Figure 10:
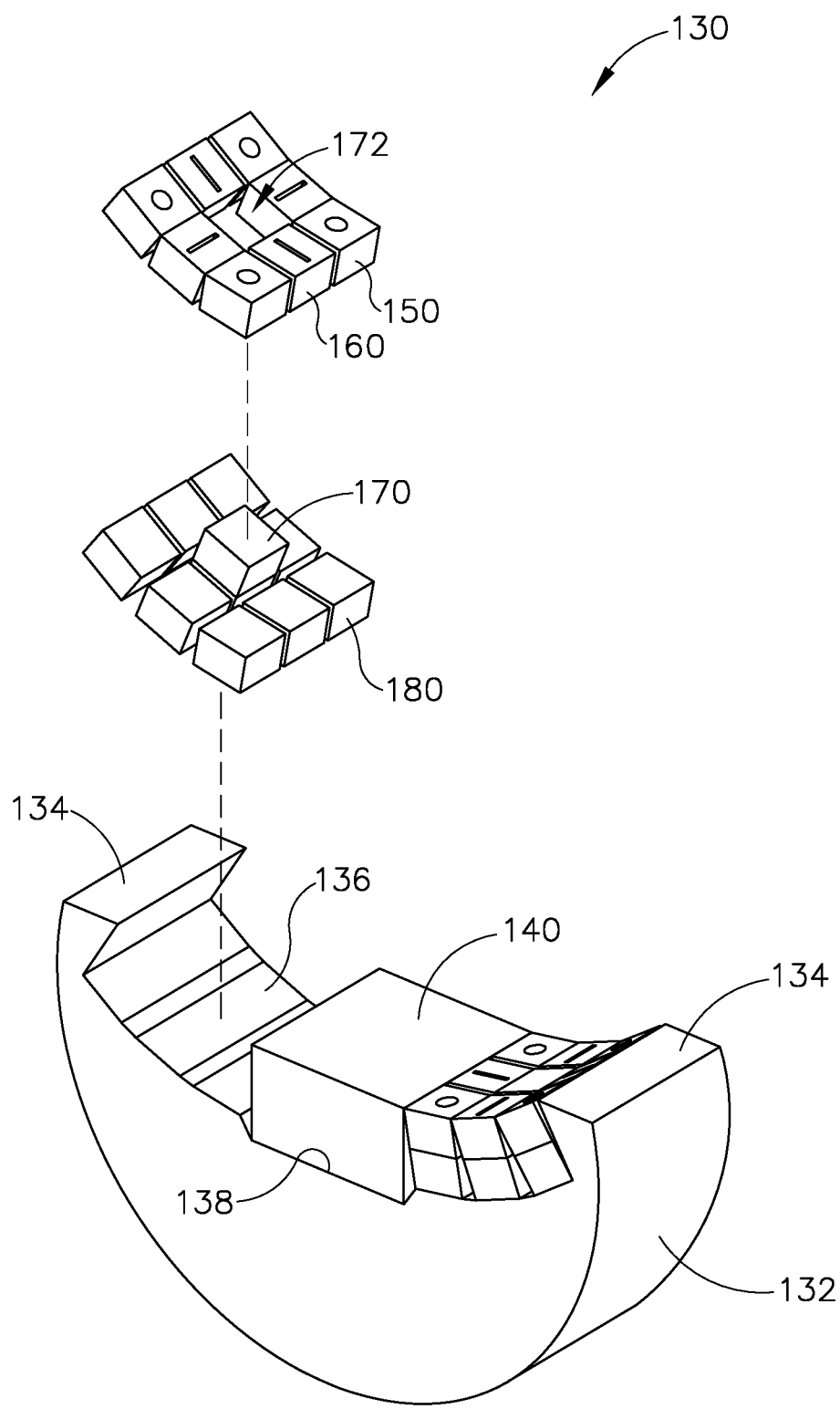
FIG. 10 depicts a partially exploded perspective view of the subassembly of FIG. 8.

As best seen in FIGS. 4, 8, and 10, each subassembly (130) includes a body (132), two arrays of light sources (180), two arrays of collimators (150, 160), a pair of primary light sources (170), and an image sensor assembly (140). Body (132) defines a recessed surface (136) that supports light sources (180) and primary light sources (170), with a central flat region (138) that supports image sensor assembly (140). Fingers (134) are positioned at opposing ends of recessed surface (136), similar to fingers (124) described above. Light sources (180) of subassembly (130) are configured and operable just like light sources (180) of subassembly (120) as described above. However, unlike light sources (180) of subassembly (120), each array of light sources (180) of subassembly (130) are arranged in a square pattern with primary light source (170) positioned at the center of the square. Similarly, collimators (150, 160) of subassembly (130) are configured and operable just like collimators (150, 160) of subassembly (120) as described above; though collimators (150, 160) of subassembly (130) are arranged in a square pattern complementing the square pattern defined by light sources (180) of subassembly (130).

The square pattern of each collimator (150, 160) array defines a central opening (172) in which the corresponding primary light source (170) is disposed. Thus, while each light source (180) of subassembly (130) has a corresponding collimator (150, 160) positioned over the light source (180), primary light source (170) does not have any collimator (150, 160) positioned over primary light source (170). During operation as described in greater detail below, each primary light source (170) may remain constantly illuminated while light sources (180) are separately illuminated in a predefined sequence. By way of example only, primary light sources (170) may comprise LEDs. Other suitable forms that primary light sources (170) may take will be apparent to those skilled in the art in view of the teachings herein.

Each image sensor assembly (140) is operable to convert optically received images into digital form. Any suitable conventional image sensor may be used. In the present example, image sensor assembly is laterally interposed between (140) two adjacent arrays of light sources (180), collimators (150, 160), and primary light sources (170). Also in the present example, each image sensor assembly (140) is positioned to provide a line of sight that is transversely oriented relative to the longitudinal axis of shaft (42). Other suitable arrangements will be apparent to those skilled in the art in view of the teachings herein.

Also in the present example, image data captured by image sensor assemblies (140) is communicated to processor (12), which then processes the data as will be described in greater detail below. Processor (12) also communicates the power to light sources (170, 180) to drive light sources (170, 180) to emit light. Alternatively, any other suitable hardware may be used to process the image data captured by image sensor assemblies (140) and/or provide illumination power to light sources (170, 180). For instance, endoscope (40) may include an on-board power source (e.g., battery) that provides illumination power to light sources (170, 180). Other suitable arrangements for communication of image data captured by image sensor assemblies (140) and provides illumination power to light sources (170, 180) will be apparent to those skilled in the art in view of the teachings herein.

Figure 11:
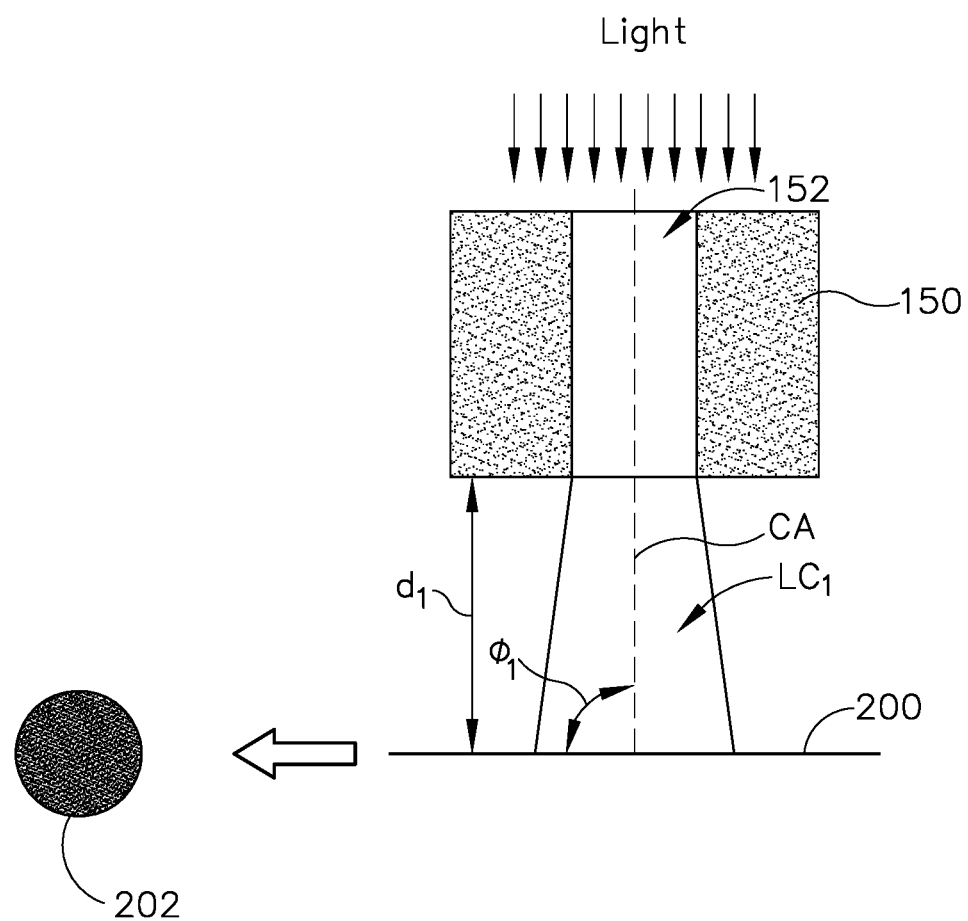
FIG. 11 depicts a diagrammatic view of light passing through the collimator of FIG. 6 to reach a first surface, with a representation of the resulting image.
Figure 12:
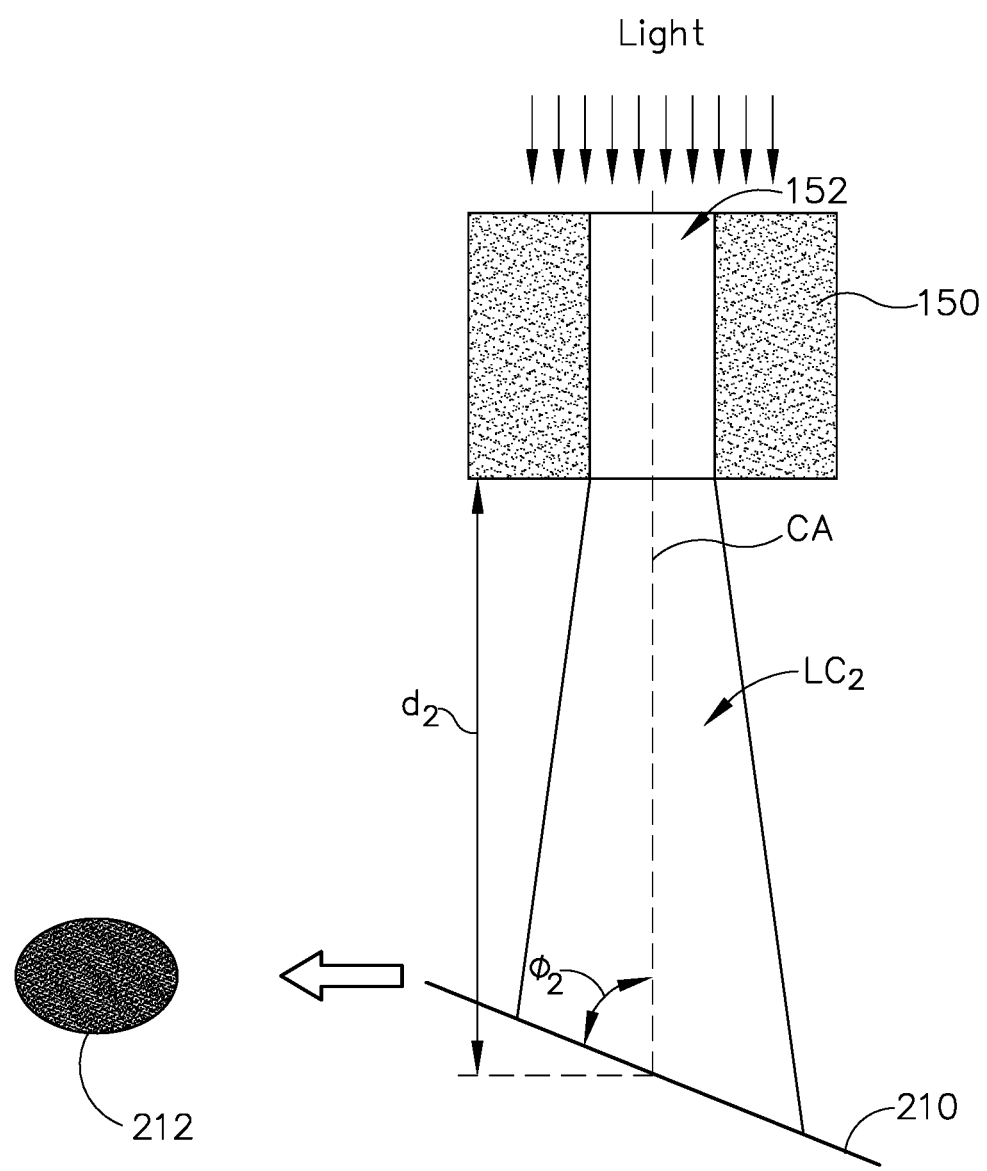
FIG. 12 depicts a diagrammatic view of light passing through the collimator of FIG. 6 to reach a second surface, with a representation of the resulting image.

FIGS. 11-12 show an example of different ways in which image sensor assembly (140) may pick up images of the surfaces of anatomical structures. For instance, FIG. 11 shows a scenario where a surface (200) of an anatomical structure is positioned at a distance ($d_1$) from the distal face of a collimator (150), with the surface (200) being oriented at an angle ($\varphi_1$) from the central axis (CA) of collimator (150). In this example, central axis (CA) of collimator (150) is oriented transversely relative to the longitudinal axis of shaft (42). The circular opening (152) of collimator (150) focuses the light emitted by light source (180) into a light cone ($LC_1$) that reaches the surface (200) of the anatomical structure. Image sensor assembly (140) picks up the correspondingly illuminated region of the surface (200) as an image (202). In the example depicted in FIG. 11, the angle ($\varphi_1$) is approximately 90°, such that image (202) is in the form of a circle.

FIG. 12 shows a scenario where a surface (210) of an anatomical structure is positioned at a distance ($d_2$) from the distal face of a collimator (150), with the surface (210) being oriented at an angle ($\varphi_2$) from the central axis (CA) of collimator (150). The circular opening (152) of collimator (150) focuses the light emitted by light source (180) into a light cone ($LC_2$) that reaches the surface (210) of the anatomical structure. Image sensor assembly (140) picks up the correspondingly illuminated region of the surface (210) as an image (212). In the example depicted in FIG. 12, the angle ($\varphi_1$) is oblique, such that image (212) is in the form of an ellipse. Thus, image (212) has an aspect ratio that differs from the aspect ratio of image (210). In view of this, those skilled in the art will appreciate that differently oriented surfaces of anatomical structures will provide differently configured illuminated regions of such surfaces, with collimators (150, 160) effectively enhancing the differences in surface orientations.

Figure 13:
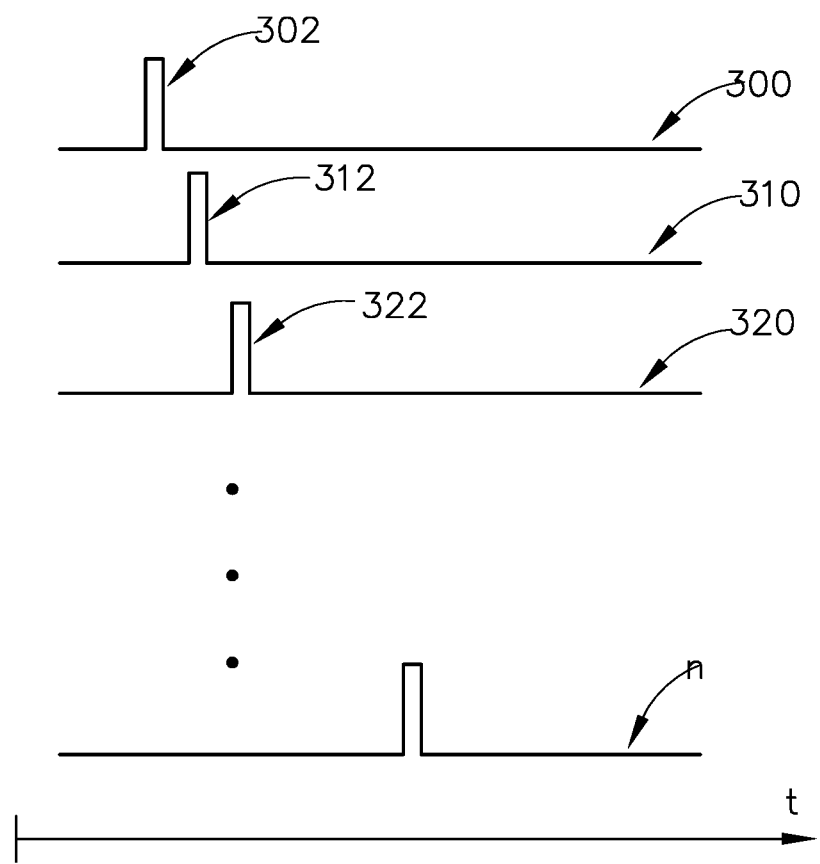
FIG. 13 depicts a diagrammatic view of an exemplary sequence of discrete light activation signals that may be used to activate respective light sources in the distal end of the endoscope of FIG. 2.

FIG. 13 shows an exemplary sequence of activations for light sources (180). In particular, a first light source (180) is temporarily activated by a power pulse (302) in a first signal (300), a second light source (180) is temporarily activated by a subsequent power pulse (312) in a second signal (310), a third light source (180) is temporarily activated by a subsequent power pulse (322) in a third signal (320), and so on. According to this scheme, light sources (180) are activated in a sequence whereby no two light sources (180) are activated simultaneously. By way of example only, the sequence may be similar to a phased array activation. Image sensor assemblies (140) may continuously capture high resolution images during this sequence. By avoiding simultaneous activation of light sources (180), imaging head (100) may avoid oversaturation of the imaging field with light. In some variations, more than one light source (180) may in fact be activated by corresponding pulses simultaneously. In some such versions, the simultaneously activated light sources (180) are at different subassemblies (120, 130) of imaging head (100). This may prevent the imaging field of each image sensor assembly (140) from getting oversaturated with light at any given time.

The components of subassemblies (120, 130) are positioned along a concave curve in recess (110) in the present example. Due to this concave arrangement of light sources (170, 180), and the relative positioning of image sensor assemblies (140), light emitted by light sources (170, 180) may generally converge along a surface positioned in front of image sensor assemblies (140). When light sources (180) are activated in a sequence as described above, the light from light sources (180) may impinge on the same surface of an anatomical structure at different angles ($\varphi$). In other words, the light from a first light source (180) (as collimated by a corresponding collimator (150, 160)), may impinge upon a surface of an anatomical structure at a first angle ($\varphi_1$); while the light from a second light source (180) (as collimated by a corresponding collimator (150, 160)), may impinge upon the same surface of the same anatomical structure at a second angle ($\varphi_2$), due to the different positioning of light sources (180) relative to that surface. If the first light source (180) is illuminated first, the corresponding image sensor assembly (140) may capture a corresponding image having a first aspect ratio (e.g., similar to image (202)). If the second light source (180) is illuminated second, the corresponding image sensor assembly (140) may capture a corresponding image having a second aspect ratio (e.g., similar to image (212)). Since each light source (180) and corresponding collimator (150, 160) has a differently positioned collimator axis (CA), the angle of incidence on the surface of the anatomical structure may vary for each combination of light source (180) and corresponding collimator (150, 160). These differences may result in different aspect ratios, shapes, and/or sizes (and/or other optically perceivable differences) in images captured by the corresponding image sensor assembly (140), where such images are captured of the same surface of the same anatomical structure.

Each image sensor assembly (140) may thus capture a series of images of the same surface of the same anatomical structure, with each image of the series being captured at the time a single light source (180) is activated. Processor (12) may process these images and determine the distance (d) and orientation ($\varphi$) of the surface of the anatomical structure based on the differences in the aspect ratios (or other optically perceivable differences). Processor (12) may further interpolate the surface profile of the regions of the anatomical structure surface between the regions where light was projected from light sources (180). The surface topography determined by processor (12) may be used to develop a 3D digital model of the imaged anatomical structure.

Figure 14:
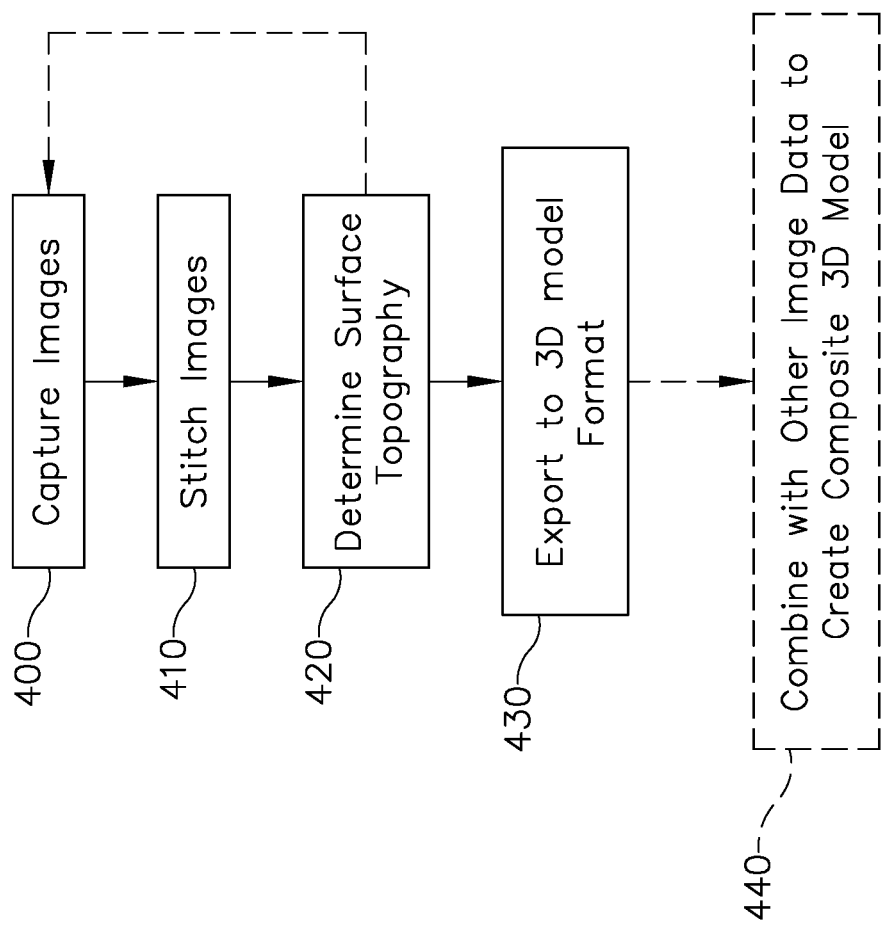
FIG. 14 depicts a flow chart of an exemplary method that may be carried out using the endoscope of FIG. 2.

FIG. 14 shows an exemplary set of steps that may be performed using endoscope (40). These steps may be performed by processor (12) and/or by any other hardware as will be apparent to those skilled in the art in view of the teachings herein. As a first step, image sensor assemblies (140) may be used to capture images (block 400) as noted above. This image capture operation (400) may be performed before a medical procedure is performed within a head (H) of a patient (P), to gather preoperative data about the anatomy within the head (H). In versions where endoscope (40) includes position sensor (50), the operator may rely on corresponding guidance provided by IGS navigation system (10) to assist in the maneuvering and positioning of imaging head (100) in the head (H) of the patient (P).

After images have been captured with imaging head (100), the captured images may be stitched together (block 410) using known image stitching techniques. Next, processor (12) may determine the surface topography (block 420) of the imaged anatomical structure as noted above. In some variations, the surface topography is determined (block 420) first, followed by the stitching (block 410). Also in some variations, the operator may make several passes over the targeted anatomical structure with imaging head (100). This may allow the acquisition of additional image data with more angles of incidence from the light sources (180) and corresponding collimators (150, 160), thereby providing additional data for processor (12) to establish the surface topography, thereby enabling processor (12) to craft a 3D digital model with greater precision and accuracy. The steps associated with blocks 400, 410, 420 may thus be reiterated as many times as desired, allowing previously captured data to be refined by subsequently captured data.

Once the desired images have been captured (block 400) and stitched (410), and the surface topography has been determined (block 420), processor (12) may synthesize this data to form a 3D digital model (block 430) of the anatomical structure. By way of example only, the final 3D digital model may be in the form of an STL file.

A 3D digital model that has been generated based on image data captured with imaging head (100) may be used in numerous ways. For instance, IGS navigation system (10) (or some other computer system) may allow an operator to explore the digital model to get a better sense of the anatomical surface layout within the head (H) of the patient (P). IGS navigation system (10) (or some other computer system) may also allow an operator to digitally manipulate the anatomy within the head (H) of the patient (P). By way of example only, software may allow the operator to model different surgical procedures (e.g., turbinate reduction, sinuplasty, septoplasty, etc.), predicting the outcomes (e.g., flow rates and other characteristics of fluid flow within the nasal cavity) for such surgical procedures. Such surgical procedure modeling may enable the physician to virtually test various different surgical procedures as potential solutions for an undesirable condition in the patient, thereby enabling the physician to identify the most optimal solution based on the modeled outcomes.

As another merely illustrative example, a 3D digital model that has been generated based on image data captured with imaging head (100) may be combined with other preoperative image data (e.g., CT scans, MRI scans, etc.) to create a composite 3D digital model or to otherwise refine a preexisting digital model. In versions where endoscope (40) includes position sensor (50), the image data may have already been correlated with spatial position data as acquired through IGS navigation system (10); and this position data correlation may further facilitate matching of data captured from imaging head (100) with data captured from other preoperative sources (e.g., CT scanner, MRI scanner, etc.). In versions where image data captured with imaging head (100) is combined with other preoperative image data (e.g., CT scans, MRI scans, etc.) to create a composite 3D digital model, additional preoperative image data may be factored in before or during the step of exporting to a 3D model format (block 430) as shown in FIG. 14. Alternatively, a 3D digital model may first be created (block 430) based on image data captured with imaging head (100); and then the other preoperative image data may be combined in with that 3D digital model to generate a composite 3D digital model (block 440).

Various suitable ways in which a composite 3D digital model may be created based on image data captured with imaging head (100) and other preoperative image data (e.g., CT scans, MRI scans, etc.) will be apparent to those skilled in the art in view of the teachings herein. By way of example only, such data may be combined to generate a composite 3D digital model in accordance with at least some of the teachings of U.S. Pat. No. 8,199,988, entitled "Method and Apparatus for Combining 3D Dental Scans with Other 3D Data Sets," issued Jun. 12, 2012, the disclosure of which is incorporated by reference herein; and/or "U.S. Pat. No. 8,821,158, entitled "Method and Apparatus for Matching Digital Three-Dimensional Dental Models with Digital Three-Dimensional Cranio-Facial CAT Scan Records," issued Sep. 2, 2014, the disclosure of which is incorporated by reference herein.

While the foregoing example describes endoscope (40) as being used to capture images to generate a preoperative 3D digital model, the same steps may also be performed after completion of a medical procedure, particularly when the medical procedure results in some kind of remodeling of an anatomical structure. Thus, endoscope (40) may be used to capture images that are used to generate a postoperative 3D digital model using the same steps described above in relation to the preoperative 3D digital model. In such scenarios, processor (12) (or some other hardware) may be used to compare the postoperative 3D digital model to the preoperative 3D digital model to determine whether the medical procedure was successful. Various ways in which a postoperative 3D digital model to the preoperative 3D digital model to determine whether the medical procedure was successful will be apparent to those skilled in the art in view of the teachings herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

An apparatus comprising: (a) a shaft defining a longitudinal axis, the shaft including: (i) a proximal end, (ii) a distal end, the distal end of the shaft being sized to fit through a human nostril into a human nasal cavity, and (iii) a flexible portion; (b) an imaging head positioned at the distal end of the shaft, the imaging head including: (i) a first image sensor assembly, (ii) a plurality of light sources, at least some of the light sources being positioned adjacent to the first image sensor assembly, the light sources being configured to be activated in a predetermined sequence, (iii) a plurality of collimators, each collimator being positioned over a corresponding light source of the plurality of light sources; and (c) a processor in communication with the imaging head, the processor being configured to activate the light sources in a predetermined sequence, the first image sensor assembly being configured to capture images of a surface illuminated by the light sources as the light sources are activated in the predetermined sequence.

EXAMPLE 2

The apparatus of Example 1, the flexible portion of the shaft being steerable to thereby enable active deflection of the imaging head away from the longitudinal axis of the shaft.

EXAMPLE 3

The apparatus of any one or more of Examples 1 through 2, the first image sensor assembly being positioned to provide a line of sight that is transversely oriented relative to the longitudinal axis of the shaft.

EXAMPLE 4

The apparatus of any one or more of Examples 1 through 3, each light source being positioned to project light along a path that is transversely oriented relative to the longitudinal axis of the shaft.

EXAMPLE 5

The apparatus of any one or more of Examples 1 through 4, each collimator defining an opening centered on a corresponding collimator central axis that is transversely oriented relative to the longitudinal axis of the shaft, each collimator being positioned to collimate light from the corresponding light source along the collimator central axis.

EXAMPLE 6

The apparatus of any one or more of Examples 1 through 4, the imaging head further including a second image sensor assembly, at least some of the light sources being positioned adjacent to the first image sensor assembly.

EXAMPLE 7

The apparatus of any one or more of Examples 1 through 6, the first image sensor assembly being located at a first longitudinal position, the second image sensor assembly being located at a second longitudinal position, wherein the second longitudinal position is proximal to the first longitudinal position.

EXAMPLE 8

The apparatus of any one or more of Examples 1 through 7, the light sources comprising LEDs.

EXAMPLE 9

The apparatus of any one or more of Examples 1 through 8, the collimators including a first set of collimators defining circular openings.

EXAMPLE 10

The apparatus of any one or more of Examples 1 through 8, the collimators including a first set of collimators defining rectangular openings.

EXAMPLE 11

The apparatus of any one or more of Examples 1 through 8, the collimators including: (i) a first set of collimators defining circular openings, and (ii) a second set of collimators defining rectangular openings.

EXAMPLE 12

The apparatus of Example 11, the collimators being arranged such that the collimators defining circular openings are alternatingly positioned between the collimators defining rectangular openings.

EXAMPLE 13

The apparatus of any one or more of Examples 1 through 12, the processor being positioned within the shaft.

EXAMPLE 14

The apparatus of any one or more of Examples 1 through 12, the processor being positioned within the imaging head.

EXAMPLE 15

The apparatus of any one or more of Examples 1 through 14, the processor being further configured to determine surface topography of an anatomical structure in a patient's head based on images captured by the first image sensor assembly.

EXAMPLE 16

The apparatus of any one or more of Examples 1 through 15, the processor being further configured to generate a three-dimensional digital model of an anatomical structure in a patient's head based on images captured by the first image sensor assembly.

EXAMPLE 17

The apparatus of Example 16, the processor being further configured to combine data from images captured by the first image sensor assembly with data from images captured through another imaging device to generate the three-dimensional digital model.

EXAMPLE 18

The apparatus of any one or more of Examples 1 through 17, the imaging head further including a position sensor configured to generate a signal indicating a position of the imaging head in three-dimensional space.

EXAMPLE 19

An apparatus comprising: (a) a shaft defining a longitudinal axis, the shaft including: (i) a proximal end, (ii) a distal end, the distal end of the shaft being sized to fit through a human nostril into a human nasal cavity, and (iii) a flexible portion; and (b) an imaging head positioned at the distal end of the shaft, the imaging head including: (i) an image sensor assembly positioned to provide a line of sight that is transversely oriented relative to the longitudinal axis of the shaft, (ii) a plurality of light sources positioned adjacent to the first image sensor assembly, each light source being positioned to project light along a path that is transversely oriented relative to the longitudinal axis of the shaft, (iii) a first set of collimators, each collimator of the first set of collimators being positioned over a corresponding light source of the plurality of light sources, each collimator of the first set defining an opening having a first shape, each collimator of the first set being positioned to collimate light from the corresponding light source along a path that is transversely oriented relative to the longitudinal axis of the shaft, and (iv) a second set of collimators, each collimator of the second set of collimators being positioned over a corresponding light source of the plurality of light sources, each collimator of the second set defining an opening having a second shape, each collimator of the second set being positioned to collimate light from the corresponding light source along a path that is transversely oriented relative to the longitudinal axis of the shaft.

EXAMPLE 20

A method comprising: (a) activating a plurality of light sources at the distal end of a shaft positioned in a nasal cavity of a patient, the light sources emitting light through respective collimators, the light sources being activated in a sequence; (b) capturing images of an anatomical structure illuminated by the light sources, each image corresponding to a region of the anatomical structure as illuminated by a corresponding light source such that each image is associated with a corresponding light source of the plurality of light sources; (c) determining surface topography of the anatomical structure based on the captured images; and (d) generating a three-dimensional digital model based on the captured image and determined surface topography.

IV. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a shaft defining a longitudinal axis, the shaft including:
      (i) a proximal end,
      (ii) a distal end, the distal end of the shaft being sized to fit through a human nostril into a human nasal cavity, and
      (iii) a flexible portion;
   (b) an imaging head positioned at the distal end of the shaft, the imaging head including:
      (i) a first image sensor assembly,
      (ii) a plurality of light sources, at least some of the light sources being positioned adjacent to the first image sensor assembly, the light sources being configured to be activated in a predetermined sequence, and
      (iii) a plurality of collimators, each collimator being positioned over a corresponding light source of the plurality of light sources, each collimator defining an aperture centered on a corresponding collimator central axis that is transversely oriented relative to the longitudinal axis of the shaft, each collimator being positioned to collimate light from the corresponding light source along the collimator central axis; and (c) a processor in communication with the imaging head, the processor being configured to activate the light sources in the predetermined sequence, the first image sensor assembly being configured to capture images of a surface illuminated by the light sources as the light sources are activated in the predetermined sequence.

2. The apparatus of claim 1, the flexible portion of the shaft being steerable to thereby enable active deflection of the imaging head away from the longitudinal axis of the shaft.

3. The apparatus of claim 1, the first image sensor assembly being positioned to provide a line of sight that is transversely oriented relative to the longitudinal axis of the shaft.

4. The apparatus of claim 1, each light source being positioned to project light along a path that is transversely oriented relative to the longitudinal axis of the shaft.

5. The apparatus of claim 1, the imaging head further including a second image sensor assembly, at least some of the light sources being positioned adjacent to the first image sensor assembly.

6. The apparatus of claim 5, the first image sensor assembly being located at a first longitudinal position, the second image sensor assembly being located at a second longitudinal position, wherein the second longitudinal position is proximal to the first longitudinal position.

7. The apparatus of claim 1, the light sources comprising LEDs.

8. The apparatus of claim 1, the collimators including a first set of collimators defining circular apertures.

9. The apparatus of claim 1, the collimators including a first set of collimators defining rectangular apertures.

10. The apparatus of claim 1, the collimators including:
(i) a first set of collimators defining circular apertures, and
(ii) a second set of collimators defining rectangular apertures.

11. The apparatus of claim 10, the collimators being arranged such that the collimators defining circular apertures are alternatingly positioned between the collimators defining rectangular apertures.

12. The apparatus of claim 1, the processor being positioned within the shaft.

13. The apparatus of claim 1, the processor being positioned within the imaging head.

14. The apparatus of claim 1, the processor being further configured to determine surface topography of an anatomical structure in a patient's head based on images captured by the first image sensor assembly.

15. The apparatus of claim 1, the processor being further configured to generate a three-dimensional digital model of an anatomical structure in a patient's head based on images captured by the first image sensor assembly.

16. The apparatus of claim 15, the processor being further configured to combine data from images captured by the first image sensor assembly with data from images captured through another imaging device to generate the three-dimensional digital model.

17. The apparatus of claim 1, the imaging head further including a position sensor configured to generate a signal indicating a position of the imaging head in three-dimensional space.

18. An apparatus comprising:
(a) a body including a flexible portion and a distal end, the distal end of the body being sized to fit through a human nostril into a human nasal cavity,
(b) an imaging head positioned at the distal end of the body, the imaging head including:
(i) at least one image sensor assembly,
(ii) a plurality of light sources, at least some of the light sources being positioned adjacent to the at least one image sensor assembly, and
(iii) a plurality of collimators, each collimator being positioned over a corresponding light source of the plurality of light sources, each collimator defining a bore centered on a corresponding collimator central axis that is transversely oriented relative to the longitudinal axis of the shaft, each collimator being positioned to collimate light from the corresponding light source along the collimator central axis; and
(c) a processor in communication with the imaging head, the processor being configured to activate the light sources in a predetermined sequence, the at least one image sensor assembly being configured to capture images of a surface illuminated by the light sources as the light sources are activated in the predetermined sequence.

19. An apparatus comprising:
(a) a shaft defining a longitudinal axis, the shaft including:
(i) a proximal end,
(ii) a distal end, the distal end of the shaft being sized to fit through a human nostril into a human nasal cavity, and
(iii) a flexible portion;
(b) an imaging head positioned at the distal end of the shaft, the imaging head including:
(i) at least one image sensor assembly,
(ii) a plurality of light sources, and
(iii) a plurality of collimators, each collimator being positioned over a corresponding light source of the plurality of light sources, each collimator defining a bore centered on a corresponding collimator central axis that is transversely oriented relative to the longitudinal axis of the shaft, each collimator being positioned to collimate light from the corresponding light source along the collimator central axis; and
(c) a processor in communication with the imaging head, the processor being configured to activate the light sources in a predetermined sequence, the at least one image sensor assembly being configured to capture images of a surface illuminated by the light sources as the light sources are activated in the predetermined sequence.

20. The apparatus of claim 19, the distal end being sized to fit through the human nostril into the human nasal cavity for positioning the imaging head to observe at least one of paranasal sinus ostia, a frontal recess, Eustachian tube openings, or nasal turbinates.

* * * * *